United States Patent [19]

Bourbon et al.

[11] Patent Number: 5,662,941

[45] Date of Patent: Sep. 2, 1997

[54] METHOD FOR TREATING DISEASES CAUSED BY BACTERIAL MICROORGANISMS WITH A COMPOSITION CONTAINING FLUORINE F– AND LITHIUM LI+

[76] Inventors: Pierre Bourbon, 36, rue Volta, 31000, Toulouse, France; Pierre Lagny, Castle Town Court 6, Celbridge, C/O Kildare, Ireland; Pierre Billot, 20 bd. de la Saussaye, 92200 Neuilly/Seine, France

[21] Appl. No.: 125,526

[22] Filed: Sep. 22, 1993

Related U.S. Application Data

[63] Continuation of Ser. No. 691,472, Apr. 25, 1991, abandoned, which is a continuation-in-part of Ser. No. 246,982, Sep. 20, 1988, Pat. No. 5,063,064.

[30] Foreign Application Priority Data

Sep. 22, 1987 [FR] France .................................. 87 13086

[51] Int. Cl.⁶ .................................................. A61K 33/14
[52] U.S. Cl. ............................................. 424/673; 514/931
[58] Field of Search ................................ 424/673; 514/931

[56] References Cited

U.S. PATENT DOCUMENTS

| | | | |
|---|---|---|---|
| 4,097,590 | 6/1978 | Weisz | 424/151 |
| 4,321,277 | 3/1982 | Saurino | 514/643 |
| 4,473,547 | 9/1984 | Sipos | 424/152 |
| 5,026,561 | 6/1991 | Bourbon et al. | 424/673 |
| 5,063,064 | 11/1991 | Bourbon et al. | 424/673 |

*Primary Examiner*—Kevin E. Weddington
*Attorney, Agent, or Firm*—Young & Thompson

[57] ABSTRACT

The invention is directed to a composition and a method for using the same which composition inhibits or destroys unicellular living organisms. The composition is particularly effective in combating sexually transmitted diseases and as an antiseptic agent. The composition of the invention comprises lithium and ionic or ionizable, fluorine, for example, lithium fluoride. A suitable excipient such as KATHON may also be present.

12 Claims, No Drawings

METHOD FOR TREATING DISEASES CAUSED BY BACTERIAL MICROORGANISMS WITH A COMPOSITION CONTAINING FLUORINE F– AND LITHIUM LI+

This application is a continuation of application Ser. No. 07/691,472 filed Apr. 25, 1997, now abandoned, which is a continuation-in-part of application Ser. No. 246,982 filed Sep. 20, 1988, now U.S. Pat. No. 5,063,064 the disclosure of which application is expressly incorporated herein by reference.

BACKGROUND OF THE INVENTION

The invention relates to the inhibition or destruction of unicellular living organisms such as protozoa, microbes bacteria, gametes, fungi, yeasts or the like, and viruses. It hence relates especially to the technical fields of local contraception, of antibiotic therapy and of antisepsis, whether in the context of pharmacy or of cosmetics, as well as to that of disinfection.

Many substances and compositions that inhibit or destroy unicellular living organisms are already known. Unpublished European Patent Application No. 86/402,716.4, filed on 8 Dec. 1986 and U.S. patent application Ser. No. 07/053,374 filed on 22 May 1987 by the applicant, mention such substances and compositions, and already teach that it is advantageous to use a compound that liberates F– ions alone or in combination with another primary active principle.

Moreover, lithium in the ionic state is already known in various therapeutic applications: in neurology, by way of a normothymic agent, in rhumatology or urology, by way of a uric acid-eliminating gent, in the field of dental car, by way of antiseptic PYOREX, registered trademark), and in the treatment of conditions of the airways in pneumology (THIOPHEOL).

Lithium fluoride is also already known as a chemical compound (The MERCK INDEX, TENTH EDITION, page 793, reference 5357). This compound is not, however, used by way of a medicinal product, or for inhibiting or destroying unicellular living organisms.

European Patent Application 0 055 109 describes an anti-caries composition comprising a fluorine slat and a carbohydrate. Among fluorides used by way of an anti-caries agent, lithium fluoride is mentioned. However, this document does not draw attention to any particular property due to the lithium fluoride for inhibiting or destroying microorganisms. In effect, in the combating of dental caries, fluorine has a known action, which does not consist in inhibiting or destroying microorganisms.

European Patent Application 0,162,574 describes a composition for oral/dental hygiene, such as a dentifrice, comprising a fluorine salt, a zinc salt, a buffering agent and an excipient. Among the fluorine slats referred to lithium fluoride is mentioned. However, the fluorine salts are used in the context of that document only by way of anti-caries agent, as is taught in European Patent Application 0,055,109. Moreover, European Patent Application 0,162,574 also mentions the possibility of using a cationic surfactant agent by way of an antiseptic and antibacterial. However, this document does not describe a composition that makes it possible to inhibit or destroy microorganisms containing lithium fluoride.

the objects of the invention are to remedy the known drawbacks of the prior art, namely:

to reduce the necessary concentrations of active principles and/or activating principles while retaining the same efficacy, in order to limit or avoid side effects, to propose a composition that inhibits or destroys unicellular living organisms and which is safely administrable systemically or parenterally, to provide a new compound which is usable by way of a medicinal product or bactericidal, antibiotic, virucidal, antiseptic or disinfectant product or contraceptive, to propose other therapeutic applications of ionic lithium, and to provide a composition which is active against certain pathogenic organisms against which no remedy is known.

THE SUMMARY OF THE INVENTION

The invention hence proposes a spermicidal composition, a composition enabling sexually transmitted diseases to be combated, an antiseptic composition for the local disinfection of the human body—in particular of the skin, the mucosae, the limbs, etc—a composition for the disinfection of surfaces such as floors or instruments, and an antibiotic composition, and more generally a composition intended for destroying or inhibiting unicellular living organisms such as protozoa, microbes, bacteria, gametes, fungi, yeasts, viruses or the like, in therapeutic, contraceptive, sanitary or agricultural applications, characterized in that they contain:

ionic or ionisable lithium, or ionic or ionisable lithium and ionic or ionisable fluorine, in particular lithium fluoride, or A) lithium fluoride and B) a suitable excipient, or A) lithium fluoride, B) an active principle suitable for the application in quesiton—in particular a surfactant detergent such as a quaternary ammonium compound, for example benzalkonium chloride, or a nonoxinol, or an antibiotic or a bactericide, or a sporicide, or a fungicide, or a virucide, or an antiseptic, or a disinfectant, or a spermicide—and C) a suitable excipient, or A) lithium fluoride, B) an active principle suitable for the application in question—in particular as referred to about—, C) a preservative agent such as KATHON CG (registered trademark) and D) a suitable excipient.

A composition according to the invention can also contain in addition, another fluorine salt, in particular sodium fluoride.

The invention also proposes a pharmaceutical composition containing ionic and ionisable fluorine and ionic or ionisable lithium, in particular lithium fluoride. The invention also proposes such a composition containing in addition, an active principle suitable for the therapeutic application in question—in particular a surfactant detergent such as quaternary ammonium compound, for example benzalkonium chloride or a nonoxinol, or an antibiotic, or a bactericide, or a spermicide, or a fungicide, or a virucide. The invention also proposes such a composition containing, in addition, an active principle with the exception of a zinc salt.

The invention also relates to the application of lithium Li+ cations for manufacturing a product intended for destroying or inhibiting gametes—in particular spermatozoa—by way of a local contraceptive.

The invention also relates to the application of at least one compound capable of liberating F– ions and Li+ ions—in particular lithium fluoride—for manufacturing a composition intended for combating sexually transmitted diseases.

The invention also relates to the application of at least one compound capable of liberating F– ions and Li+ ions—in particular lithium fluoride—for manufacturing an antibiotic composition.

The invention also relates to the application of at least one compound capable of liberating F– ions and Li+ ions—in particular lithium fluoride—for manufacturing an antiseptic or disinfectant composition.

The invention also relates to the application at least one compound capable of liberating F– ions, at least one compound capable of liberating Li+ ions—in particular lithium fluoride—and at least one active principle—in particular a surfactant detergent such as a quaternary ammonium compound, for example benzalkonium chloride, or a nonoxinol—for manufacturing a spermicidal composition.

The invention also relates to the application of at least one compound capable of liberating F– ions, at least one compound capable of liberating Li+ ions—in particular lithium fluoride—and at least one active principle—in particular a surfacant detergent such as a quaternary ammonium compound, for example benzalkonium chloride, or a nonoxinol—for manufacturing a compound intended for combating sexually transmitted diseases.

The invention also relates to the application of at least one compound capable of liberating F– ions, at least one compound capable of liberating Li+ ions—in particular lithium fluoride—and at least one active principle—in particular a surfactant detergent such as a quaternary ammonium compound, for example benzalkonium chloride, or a nonoxinol—for manufacturing an antiseptic or disinfectant composition.

The invention also relates to the application of at least one compound capable of liberating F– ions, at least one compound capable of liberating Li+ ions—in particular lithium fluoride—and at least one antibiotic principle for manufacturing an antibiotic product containing sufficiently low concentrations of F–, Li+ and antibiotic principle to enable it to be administered orally or parenterally.

The invention also relates to the application of at least one compound capable of liberating F– ions, at least one compound capable of liberating Li+ ions—in particular lithium fluoride—at least one virucidal principle—in particular a surfactant detergent such as a quaternary ammonium compound, for example benzalkonium chloride—for manufacturing a virucidal product containing sufficiently low concentrations of F–, Li+ and primary virucidal principle to enable it to be administered orally or parenterally.

The invention also relates to the application of at least one compound capable of liberating F– ions, at least one compound capable of liberating Li+ ions—in particular lithium fluoride—and at least one bactericidal or antibiotic or fungicidal principle, for manufacturing a composition intended for combating pathogenic microorganisms such as chlamydiae, *Gardnerella vaginalis,* Ducrey's bacillus, *Candida albicans,* Aspergillus, Streptococcus, *Proteus vulgaris, Haemophilus influenzae, Pseudomonas aeruginosa, Escherichia coli,* Staphylococcus, Mycobacterium, *Neisseria gonorrhoeae,* Trichomonas, Treponema, *Sarcina lutea, Bacillus subtilis, Klebsiella pneumoniae* and Enterococcus.

The invention hence demonstrates, on the one hand, the surprising synergistic effect of the combination of F– anions with Li+ cations for destroying or inhibiting unicellular living organisms, and by way of a medicinal product, contraceptive, cosmetic, bactericide, antibiotic, virucide or disinfectant, on the other hand, new applications given to Li+ ions, and finally a surprising activity of the combination of F–, Li+ and a primary active principle, enabling the concentrations to be reduced considerably and, in particular, products that are usable orally or parenterally to be obtained.

The invention also consists in having selected lithium fluoride among the possible fluorides mentioned in the prior art, an in having qualitatively and quantitatively demonstrated unexpected properties of lithium fluoride.

EXAMPLES AND PREFERRED EMBODIMENTS

The invention is illustrated by the examples below; the terminology and the methodologies used below have already been defined in unpublished European Patent Application No. 86/402,716.4, filed on 8 Dec. 1986 and U.S. patent application 07/053,374 filed on 22 May 1987 by the application, and are integrated in the present specification and will hence not be fully specified again.

A benzalkonium chloride solution used in the trials contained a minimum of 90% by weight of C14 benzalkonium chloride of formula:

$(C_6H_5-CH_2-CH_3NCH_3-C_{14}H_{29}+.Cl^-)$ or myristyldimethylbenzylammonium chloride. It is also possible to use cocodimethylbenzylammonium chloride or alkyldimethylbenzylammonium chloride, or another quaternary ammonium chloride. All the percentages given are percentages by weight.

KATHON CG (registered trademark) is a known preservative marketed by ROHM AND HAAS COMPANY (U.S.A.), and consisting of a mixture of two isothiazolines identified according to IUPAC nomenclature as 5-chloro 2-methyl-4-isothiazolin-3-one and 2-methyl-4 isothiaxolin-3-one.

I—APPLICATION OF THE INVENTION IN THE FIELD OF LOCAL CONTRACEPTION

Example 1

European Patent Application No. 86/402,716.4 showed that F– ions alone have a MIC (minimal inhibitory concentration), according to the SANDERS-CRAMER total spermicidal test according to IPPP standards of 5 ppm, equivalent to 0.0005%.

The same test carried out with lithium fluoride Lif alone showed that lithium fluoride alone has a MIC of the order of 3 ppm, equivalent to 0.0003%.

The same test carried out with lithium chloride LiCl alone showed that lithium chloride alone has a MIC of 20 ppm, equivalent to 0.002%.

A spermicidal effect of Li+ ions is hence observed. However, above all, the combination F–/Li+ achieves an unexpected synergistic effect.

The proportions of lithium fluoride contained in a spermicidal composition according to the invention must be such that the titre of lithium fluoride which it can liberate in vivo is greater than 2.5 mg/l, in order to be effective without reaching doses that cause side reactions.

The proportions liberated in vivo depend, of course, on the galenical form used. For example, the following galenical forms yield good results: cream, jelly, pessary, pad, soluble sheet, tablet, foam. For example:

| GALENICAL FORM | LiF (% by weight) |
|---|---|
| CREAM | 0.55 |

Example 2

Furthermore, European Patent Application No. 86/402,716.4 showed that the addition of 1 milliliter of solution containing 0.0001% of F− anions (for example in the form of sodium fluoride) to 1 milliliter of composition containing benzalkonium chloride as primary active principle, in the context of the total spermicidal test according to IPPF standards, enables the MIC of the benzalkonium chloride to be lowered from a value of 0.006% (in the initial 1 milliliter) to 0.002% (in the initial 1 milliliter).

The same test carried out (in vitro) replacing the solution of 1 milliliter containing 0.0001% of F− anions by a solution of 1 milliliter containing 0.0001% of lithium fluoride enabled a MIC of benzalkonium chloride of 0.0009% (in the initial 1 milliliter) to be obtained.

A further boosting effect is hence observed. The maximal results (in vitro) were obtained with a solution of lithium fluoride at a concentration of 0.0001%.

The following galenical forms may be used: cream, jelly, pessary, pad, soluble sheet, tablet, foam. For example:

CREAM:
  bensalkonium chloride 0.90%
  LiF 0.55%
  excipients: emulsive agent, preservative such as KATHON (registered trademark), purified water, perfume qs. 100%.
JELLY: sameformulations as the cream
  excipients: soluble derivatives of cellulose, glycerin, perservative such as KATHON (registered trademark), purified water, perfume qs. 100%.
PAD: impregnated with the cream defined above
TABLETS:
  benzalkonium chloride 0.020 g
  LiF 0.010 g
  excipients: sodium bicarbonate, citric acid, colloidal silica, cellulose, magnesium stearate, lactose qs. 1 tablet.
SOLUBLE SHEET: same formulations as the cream
  excipients: polyvinilic alcohol, glycerin, preservative such as KATHON (registered trademark), purified water qs. 100%.
PESSARIES:
  benzalkonium chloride 0.017 g
  LiF 0.010 g
  excipients: semi-synthetic glycerides, preservative such as KATHON (registered trademark) qs. 1 pessary.

A local contraceptive, in particular spermicidal, product according to the invention is characterized in that it contains between 0.20% and 0.75%—in particular, of the order of 0.55%—by weight of lithium fluoride and between 0.01% and 1.20% of benzalkonium chloride.

II—APPLICATION OF THE INVENTION FOR COMBATING THE MICROORGANISMS RESPONSIBLE FOR INFECTIONS SUCH AS SEXUALLY TRANSMITTED DISEASES.

Example 3

COMBATING CHLAMYDIAE

The methodology of the tests performed in order to demonstrate the application of the invention in the context of combating chlamydiae is that described by Professors F. CATALAN, P. SEDNAOUI, A. MILOVANOVIC et al., Institut A. FOURNIER, PARIS, already mentioned in unpublished European Patent Application No. 86/402,716.4.

The test was performed on 12 strains of *Chlamydia trachomatis* originating from hospital sources, in particular from cases of urethritis. All the trials were performed in duplicate, and the results compared with those for a listed control strain.

It was first verified that lithium fluoride at a concentration of 1 mg/l does not have toxic activity with respect to MAC COY cells. In addition, since the threshold of cytotoxic activity of benzalkonium chloride is 0.01% with respect to MAC COY cells, benzalkonium chloride is not toxic either on MAC COY cells under the conditions of the trials carried out.

The MIC corresponds to the concentration of benzalkonium chloride at and above which the average number of colonies in Petri dishes containing the active substance is less than one tenth of the average number of colonies in Petri dishes without active substance.

The MIC of benzalkonium chloride alone varied with respect to the 12 wild-type strains tested, from 12 to 180 mg/l. The MIC of benzalkonium chloride with respect to the listed test strain is 18 mg/l.

The MIC of benzalkonium chloride to which 1 mg/ml of lithium fluoride has been added varied with respect to these same 12 strains tested, from 8 to 160 mg/l. The MIC of benzalkonium chloride to which 1 mg/ml has been added with respect to the listed test strain is 13 mg/l.

A big improvement of the results with lithium fluoride is hence observed.

Example 4

COMBATING *GARDNERELLA VAGINALIS*

Two trials were carried out in order to illustrate the application of the invention in combating *Gardnerella vaginalis*.

In the first trial, the sample of bactericidal substance was incorporated directly in the specific culture edium of the microorganism. A concentration series of the bactericidal substance was prepared in the geometric ratio of 2, from 400 µg/ml to 1.56 µg/ml. The cell concentration used in the seeding of the Petri dishes was $10^{-3}$ per ml. A 24-hour incubation was performed at 37° C., and then, for each wild-type strain tested, the concentration of primary principle destroying all the microorganisms (see method of Professor F. CATALAN et al., Institut A. FOURNIER, PARIS) was determined. The trial was performed on 32 wild-type strains of *Gardnerella vaginalis* originating from hospital sources and with benzalkonium chloride and then nonoxinol 9 as active principles, and with sodium fluoride NaF at a concentration of 1 mg/l and then lithium fluoride LiF at a concentration of 1 mg/l as activating principles. The results obtained are correlated in the table below. The expresses the number of strains inhibited out of the 32 tested, in terms of the concentrations of primary active principle (benzalkonium chloride or nonoxinol).

| SUBSTANCE | Concentration in mg/l of primary active principle (benzalkonium chloride or nonoxinol) | | | | | | | | |
|---|---|---|---|---|---|---|---|---|---|
| | 1.56 | 5.125 | 6.25 | 12.5 | 25 | 50 | 100 | 200 | 400 |
| Benzalkonium chloride | 0 | 0 | 1 | 28 | 31 | 32 | — | — | — |
| Benzalkonium chloride + NaF (1 mg/l) | 0 | 0 | 7 | 30 | 32 | — | — | — | — |
| Benzalkonium chloride + LiF (1 mg/l) | 0 | 0 | 13 | 32 | — | — | — | — | — |
| Nonoxinol 9 | 0 | 0 | 0 | 0 | 4 | 6 | 10 | 25 | 32 |
| Nonoxinol 9 + NaF (1 mg/l) | 0 | 0 | 0 | 1 | 12 | 20 | 26 | 31 | 32 |
| Nonoxinol 9 + LiF (1 mg/l) | 0 | 0 | 0 | 1 | 16 | 25 | 30 | 32 | — |

This table illustrates the surprising boosting effect of lithium fluoride compared with sodium fluoride. In effect, at equal concentrations, the number or same inhibited in the presence of LiF is always markedly greater than the number of strains inhibited in he presence of NaF. The totally lethal concentration for benzalkonium chloride falls from 50 mg/l when it is alone, to 25 mg/l in the presence of NaF, to 12.5 mg/l in the presence of LiF.

The second trial carried out was performed according to the contact methodology described in AFNOR standard 1 72–151, by counting the strains surviving after a 15-min active substance/microbacterial solution contact followed by a filtration on a membrane (porosity 0.22 μm).

In this trial, 26 wild-type strains of *Gardnerella vaginalis* were tested, originating from hospital sources. The starting solution contained 0.1% of benzalkonium chloride, and was then diluted to $10^{-1}$, $10^{-2}$, $10^{-3}$ and $10^{-4}$. The results are summarized in the table below, which gives the total number of strains surviving (out of the 26 tested) in terms of the dilution.

| Dilution of the 0.1% strength solution | Benzalkonium chloride alone | Benzalkonium chloride + NaF (1 mg/l) | Benzalkonium chloride + LiF (1 mg/ml) |
|---|---|---|---|
| $10^{-1}$ | 0 | 0 | 0 |
| $10^{-2}$ | 18 | 7 | 0 |
| $10^{-3}$ | 22 | 15 | 15 |
| $10^{-4}$ | 26 | 26 | 26 |

Example 5

COMBATING *TRICHOMONAS VAGINALIS*

The same methodology as in example 4 was used on 15 strains of *Trichomonas vaginalis*. The results are given in the following table, which indicates the number of strains inhibited out of the 15 tested, in terms of the concentrations of benzalkonium chloride:

| SUBSTANCE | Concentrations in mg/l of benzalkonium chloride | | | | | | | | |
|---|---|---|---|---|---|---|---|---|---|
| | 1.56 | 5.125 | 6.25 | 12.5 | 25 | 50 | 100 | 200 | 400 |
| Benzalkonium chloride | 1 | 3 | 9 | 13 | 15 | — | — | — | — |
| Benzalkonium chloride + Lif (1 mg/l) | 3 | 8 | 15 | — | — | — | — | — | — |

The MIC hence falls from 25 mg/l for benzalkonium chloride alone to 6.25 mg/l in the presence of LiF.

Example 6

The MIC of benzalkonium chloride, alone and in the presence of LiF at a concentration of 1 mg/l, was determined with respect to other wild-type strains originating from hospital sources namely Streptococcus 16 strains), *Staphylococcus aureus* (8 strains), *Salmonella typhimurium* (3 strains) and *Sarcina lutea* (1 strain).

The MIC values obtained are summarized below.

| STRAIN | Benzalkonium chloride alone | Benzalkonium chloride in the presence of LiF at 1 mg/l |
|---|---|---|
| Streptoccocus | 18–20 mg/l | 10 mg/l |
| Staphylococcus aureus | 1.56 mg/l | 0.30 mg/l |
| Salmonella typhimurium | 17 mg/l | 12 mg/l |
| Sarcina lutea | 15 mg/l | 11 mg/l |

Example 7

COMBATING DUCREY'S BACILLUS

The methodology employed is that described by Professor F. CATALAN, P. SEONAOUI, A. MILOVANOVIC et al., Institut A. FOURNIER, PARIS. The trials were performed on B wild-type strains of DUCREY'S Haemophilus. The following results were recorded with respect to these strains:

| Primary active principle | MIC of the primary active principle with respect to DUCREY's bacillus (mg/l) | | |
|---|---|---|---|
| | Primary active principle alone | in the presence of NaF (1 mg/l) | in the presence of LiF (1 mg/l) |
| Benzalkonium chloride | 100 | 85 | 65 |
| Nonoxinol 9 | 150 | 132.5 | 127.5 |

Lithium fluoride hence proves to be a markedly better activating principle than sodium fluoride.

Example 8

COMBATING *CANDIDA ALBICANS*

With the same methodology, trials were performed on hospital strains of *Candida albicans*:

| Primary active principle | MIC of the primary active table | | |
|---|---|---|---|
| | Primary active principle | in the presence of LiF at 0.96 mg/l | in the presence of LiF at 0.96 mg/l and of KATHON CG (registered trade mark) preservative at 0.234/mgl |
| Benzalkonium chloride | 50 mg/l | 135 mg/l | 2 mg/l |

Example 9

COMBATING *ASPERGILLUS NIGER*

With the same methodology, the following results were observed on hospital strains of *Aspergillus niger*:

| Primary active principle | MIC of the primary active principle | | |
|---|---|---|---|
| | Primary active principle alone | In the presence of LiF at 0.96 mg/l | In the presence of LiF at 0.96 mg/l and of KATHON CG (registered trademark) preservative at 0.234 mg/l |
| benzalkonium chloride | 50 mg/l | 135 mg/l | 100/mg/l |

Example 10

COMBATING PYOGENIC MICROORGANISMS

With the same methodology, the following results were observed on hospital strains of pyogenic microorganisms, namely 8-haemolytic streptococcus, *Proteus vulgaris*, *Haemophilus influenzae*:

| Primary active principle | | MIC of the primary active principle | | |
|---|---|---|---|---|
| | | β-Haemolytic streptococcus | Proteus vulgaris | Haemophilus influenzae |
| Benzalkonium chloride | Alone | 50 mg/l | 25 mg/l | 200 mg/l |
| | In the presence of LiF at 1 mg/l and of KATHON CG$^R$ preservative at 0.4 mg/l | 25 mg/l | 18.5 mg/l | 150 mg/l |

The preferred galenical forms which can, for example, be used for combating STD's are the same as in the application by way of a spermicide.

Nonoxinol 9 may also be sued as the active principle, for example:

PESSARY nonoxinol 0.060 mg/l

LiF 0.01 g excipients: semi-synthetic glycerides, preservative such as KATHON (registered trademark) qs. 1 pessary.

III—APPLICATION OF THE INVENTION IN THE FIELD OF ANTI-SEPSIS AND DISINFECTION:

Example 11

French standard NF T 72-150, March 1981, was followed by the trials carried out. The trials were performed on the strains defined by the AFNOR standard.

The results obtained on the strains defined by the AFNOR standard for benzalkonium chloride alone and for benzalkonium chloride with the addition of 1 mg/l of sodium fluoride were already given in unpublished European Patent Application 86/402,716.4, and have been recorded again.

These results are as follows:

| STRAIN | MINIMAL INHIBITORY CONCENTRATION (MIC) OF BENZALKONIUM CHLORIDE ALONE | MINIMAL INHIBITORY CONCENTRATION (MIC) OF BENZALKONIUM CHLORIDE IN THE PRESENCE OF NaF AT 1 mg/l |
|---|---|---|
| *Pseudomonas aeruginosa* CNCM A 22 | 31.25 mg/l | 18 mg/l |
| *Escherichia coli* CNCM 54 127 | 6.57 mg/l | 3 mg/l |
| *Staphylococcus aureus* Oxford strain CNCM 53 154 | 1.56 mg/l | 1.1 mg/l |
| *Streptococcus faecalis* CNCM 5 855 | 4 mg/l | 3.6 mg/l |
| *Mycobacterium smegmatis* CNCM7 326 | 30 mg/l | 26 mg/l |

The MIC obtained for benzalkonium chloride to which lithium fluoride was added at a concentration of 1 mg/l is as follows:

| STRAIN | MINIMAL INHIBITORY CONCENTRATION (MIC) OF BENZALKONIUM CHLORIDE IN THE PRESENCE OF LiF AT 1 mg/l |
|---|---|
| *Pseudomanas aeruginosa* CNCM A 22 | 15 mg/liter |
| *Escherichia coli* CNCM 54 127 | 2 mg/liter |
| *Staphylococcus faecalis* Oxford strain CNCM 53 154 | 1.1 mg/liter |
| *Streptococcus faecalis* CNCM 5 855 | 2.8 mg/liter |
| *Mycobacterium smegmatis* CNCM 7 326 | 22 mg/liter |

Example 12

The same trials as in example 11 were carried out on wild-type strains originating from hospital sources, namely 120 strains of Pseudomonas, 200 strains of *Escherichia coli*, 300 strains of Staphylococcus, 200 strains of Streptococcus and 50 strains of Mycobacterium.

The results obtained on the wild-type strains are summarized in the following table:

| STRAIN | MIC of benzalkonium chloride alone | MIC of benzalkonium chloride in the presence of LiF (1 mg/l) |
|---|---|---|
| *Pseudomonas aeruginosa* | 30 to 120 mg/l | 15 to 80 mg/l |
| *Escherichia coli* | 6 to 25 mg/l | 1.8 to 16 mg/l |
| *Staphylococcus aureus* | 2 to 13 mg/l | 0.8 to 8 mg/l |
| *Streptococcus faecalis* | 5 to 30 mg/l | 2.5 to 22 mg/l |
| *Mycobacterium smegmatis* | 32 to 120 mg/l | 20 to 90 mg/l |

Example 13

The same trials as in example 12 were carried out on hospital strains of various microorganisms. The results obtained are as follows:

| STRAIN | MIC of benzalkonium alone in mg/l | MIC of benzalkonium chloride in mg/l in the presence of Lif at 1 ppm |
|---|---|---|
| *Neisseria gonorrhoea* | 1.15 | 0.60 |
| *Trichomonas vaginalis* | 1.30 | 0.90 |
| *Candida albicans* | 50 | 35 |
| *Gardenerella vaginalis* | 50 | 41 |
| *Ducrey's bacillus* | 75 | 62 |
| *Streptococcus faecalis* | 15 | 9 |
| *Staphylococcus aureus* | 1.56 | 1 |
| *Aspergillus niger* | 85 | 80 |
| *Escherichia coli* | 8 | 6.5 |
| *Sarcina lutea* | 11 | 7.5 |
| *Bacillus subtilis* | 8 | 5.4 |

Example 14

Trials similar to those carried out in Examples 12 and 13 were carried out on 80 hospital strains of multi-resistant *Escherichia coli* producing plasmid β-lactamase. The results are as follows:

| | MIC of the primary active principle in mg/l | | |
|---|---|---|---|
| primary active principle | Primary active principle alone | in the presence LiF at 0.96 mg/l | in the presence of LiF at 0.96 mg/l and of KATHON CG (registered trademark) preservative at 0.47 mg/l |
| Benzalkonium chloride | 8 to 12 | 6 to 9 | 4 to 6 |

Example 15

The bactericidal activity of seven commercial local disinfectant antiseptics was compared with that of a foaming paste according to the invention, containing:

benzalkonium chloride 2%
KATHON CG (registered trademark) 0.1%
lithium fluoride 0.004%
sodium fluoride 1.5%
excipient: foaming base
and purified water qs.

The methodology is that defined by AFNOR standard 1 72–150, using the products under the conditions specified by the manufacturer as regards the concentrations and conditions of use.

In the table below, the sign + indicates that a growth of the microorganisms was observed, the sign ++ indicates that a very strong growth of the microorganisms was observed, and the sign − indicates that no growth of the microorganisms was observed.

Septivon-Lavril is a foaming solution marketed by Laboratoires CLIN MIDY (Paris, France).

Solubacter is a registered trademark denoting a foaming solution marketed by Laboratories INNOTHERA (Arcueil. France).

Cyteal is a foaming solution marketed by Laboratoires SINBIO (Paris, France).

Hibiscrub is a foaming solution marketed by I.C.I. PHARMA (Cergy, France).

Hibisprint is an alcoholic solution marketed by I.C.I. PHARMA (Cergy, France).

Hexomedine is a registered trademark denoting a non foaming solution marketed by THERAPLIX S.A. (France).

Cetavlon is an antiseptic solution marketed by I.C.I. PHARMA (Cergy, France).

The results obtained on *Escherichia coli, Staphylococcus aureus*, Streptococcus group A and Group C streptococcus are as follows:

| ANTISEPTIC TESTED | *Escherichia coli* | *Staphylococcus aureus* | Streptococcus group A | Streptococcus group C |
|---|---|---|---|---|
| Septivon-Lavril | − | ++ | − | − |
| Solubacter[R] | − | − | + | − |
| Cytéal | − | + | + | − |
| Hibiscrub | − | − | − | − |
| Hibisprint | − | + | + | + |
| Héxomédine[R] | − | − | − | − |
| Foaming paste | − | − | − | − |

-continued

| ANTI-SEPTIC TESTED | Escherichia coli | Staphylococcus aureus | Strepto-coccus group A | Strepto-coccus group C |
|---|---|---|---|---|
| according to the invention | | | | |
| Cétavlon | − | − | − | − |

Example 16

Trials similar to those in example 15, but measuring the bacteriostatic activity (capacity to halt the proliferation of the microorganisms) of the antiseptics were carried out. The foaming paste according to the invention was the same as in Example 15. The following results were obtained (with the same conventions as in Example 15):

| ANTISEPTIC PRODUCTS TESTED | 0.2 ml of innoculum contact time 10 mn | | | | 0.4 ml of innoculum contact time 20 mn | | | | 0.6 ml of innoculum contact time 30 mn | | | |
|---|---|---|---|---|---|---|---|---|---|---|---|---|
| | Distilled water | | Hard water | | Distilled water | | Hard water | | Distilled water | | Hard water | |
| | P+ | P− | P+ | P− | P+ | P− | P+ | P− | P+ | P− | P+ | P− |
| Crude cresol | S | S | S | S | R | S | S | R | R | R | R | R |
| Mercryl laurylé | R | S | R | R | R | R | R | R | R | R | R | R |
| Solubacter$^R$ | S | S | R | S | R | R | R | R | R | R | R | R |
| Foaming paste according to the invention | S | S | S | S | S | S | S | S | S | S | S | S |
| Formaldehyde | S | S | S | S | S | S | S | S | S | S | S | S |
| Héxomédine$^R$ | S | S | S | S | R | S | R | R | R | R | R | R |
| Hibisprint | S | S | S | S | S | S | R | R | R | R | R | R |
| Cétavlon | S | S | R | S | S | S | S | S | S | S | S | S |
| Zinc sulphate | R | R | R | R | R | R | R | R | R | R | R | R |

Example 17

The resistance of *Pseudomonas aeruginosa* to various reputedly bactericidal active principles or commercial antiseptics was studied in terms of the hardness of the water and the presence or absence of proteins. The same trial was carried out on the foaming paste according to the invention (see Example 15). Mercryl Lauryle is a foaming solution marketed by Laboratoires LABAZ (Paris, France).

Cresol is the name given to three isomeric phenols, ortho, meta and para, $C_7H_8O$, immediate homologues of phenol, $HO-C_6H_4-CH_3$.

In the following table, R denotes resistant (a growth of colonies was observed), S denotes sensitive (no significant growth was observed), P+ means that proteins were added to the solvent and P− means that the solvent does not contain proteins.

| ANTI-SEPTIC TESTED | Escherichia coli | Staphylococcus aureus | Strepto-coccus group A | Strepto-coccus Group C |
|---|---|---|---|---|
| Septivon-Lavril | − | + | − | − |
| Solubacter$^R$ | − | − | − | − |
| Cytéal | − | + | + | − |
| Hibiscrub | − | − | − | − |
| Hibisprint | − | + | + | − |
| Héxomédine$^R$ | − | − | − | − |
| Foaming paste according to the invention | − | − | − | − |
| Cétavlon | − | − | − | − |

The following galenical forms can be (for example, and without limitation) used by way of a dermatological local antiseptic (skin, mucosa, etc.):

FOAMING BAR:
  benzalkonium chloride 2%
  LiF 0.04%
  NaF 1.5%
  Excipients: foaming synthetic base, preservative such as KATHON (registered trademark), purified water, perfume qs. 100%

FOAMING PASTE: Same formulations as for the foaming bar, except for the excipient formulated as a paste.

MOISTURIZING CREAM:
  benzalkonium chloride 0.2%
  LiF 0.04%
  NaF 0.8%
  Excipients: emulsive agent, moisturizing principle, wheatgerm oil, sweet almond oil, liquid paraffin, preservative such as KATHON (registered trademark), purified water qs. 100%.

IV—APPLICATION OF THE INVENTION IN THE FIELD OF ANTIBIOTIC THERAPY

Example 18

The unicellular living organism chosen for the trials is *Pseudomonas aeruginosa* (wild-type strain originating from hospital sources).

The same methodology as for Examples 11 and 12 was followed. Bacteriostatic analyses were performed with a number of antibiotics belonging to benzylpenicillins, and aminopenicillins, and first and second generation cephalosporins, namely:

a carboxypenicillin: ticarcillin, three ureidopenicillins: azlocillin, piperacillin, apalcillin, five cephalosporins: cefoperazone, cefotaxime, ceftriaxone, cefsulodin, ceftazidime.

The determination of the MIC was carried out by the microdilution method in liquid medium on plates. Aqueous solutions of each antibiotic are prepared in MUELLER HIMION broth, to obtain dilutions in a geometric ratio of 2. The solvent is sterile double-distilled water.

The preparation of the bacterial inoculum is made with a culture of *Pseudomonas aeruginosa*, with agitation on a water bath at 37° C. for 4 to 6 hours, giving $10^6$ bacteria/ml.

The bacterial inoculum and the dilution of antibiotic are placed in the plates, and incubated for 18 to 24 hours at 37° C.—the MIC is read in the depressions. Of 958 strains tested, 235 proved resistant to ticarcillin. Of these 235, 69 do not produce a β-lactamase and 166 produce a β-lactamase, namely: 50% a PSE β-lactamase, 17% a TEM β-lactamase, 28% an OXA 8-lactamase and 5% a cephalosporinase.

Three trials were performed per antibiotic and per bacterial inoculum. The trials were performed first with the antibiotics alone trials A)§, and then with the addition of a dose of 1 mg/l of an aqueous solution of lithium fluoride trials b)§ to the dilution of each one in every cup of every plate.

The results of the trials are gathered in the following table:

Abbreviations used:

Tis S: sensitive to ticarcillin
Tic R: resistant to ticarcillin
βLac⁻: constitutive not producing β-lactamase
βLac⁺: constitutive producing β-lactamase
MIC: average MIC value It is thus noted that the addition of lithium fluoride comparison between trials a) and b)§ enables the MIC with respect to the Tic S and Tic R strains of almost all the antibiotics to be decreased.

Example 19

With the same methodology as above, the MIC values of benzalkonium chloride alone, in the presence of the KATHON CG (registered trademark) preservative (1 mg/l), and then in the presence of KATHON CG (registered trademark) (1 mg/l) and lithium fluoride (1 mg/l), were determined. 200 wild-type strains of *Pseudomonas aeruginosa* were tested.

The following results were observed:

| TRIAL | ANTIBIOTIC | STRAIN Tic S βLac⁻ MIC(µg/ml) | STRAIN Tic S βLac⁻ MIC(µg/ml) | STRAIN Tic R βLac⁺ MIC (µg/ml) | | | |
|---|---|---|---|---|---|---|---|
| | | | | TEM | PSE | OXA | CEPHALO-SPORINASE |
| 1) | TICARCILLIN | 32 | 512 | 1024 | 4096 | 512 | 256 |
| 2a) | AZLOCILLIN + | 8 | 32 | 64 | 64 | 64 | 128 |
| 2b) | LiF 1 mg/l | 4 | 32 | 64 | 64 | 64 | 128 |
| 3a) | PIPERACILLIN + | 8 | 16 | 64 | 128 | 64 | 128 |
| 3b) | LiF | 8 | 8 | 64 | 64 | 64 | 128 |
| 4a) | APALCILLIN + | 4 | 16 | 16 | 64 | 32 | 16 |
| 4b) | LiF | 2 | 8 | 8 | 32 | 32 | 16 |
| 5a) | CEFOPERAZONE + | 8 | 16 | 32 | 64 | 64 | 64 |
| 5b) | LiF | 4 | 16 | 32 | 32 | 64 | 64 |
| 6a) | CEFOTAXIME + | 16 | 32 | 32 | 32 | 32 | 256 |
| 6b) | LiF | 8 | 16 | 32 | 16 | 16 | 256 |
| 7a) | CEFTRIAXONE + | 16 | 32 | 32 | 32 | 32 | 256 |
| 7b) | LiF | 8 | 16 | 32 | 16 | 32 | 128 |
| 8a) | CEFSULODIN + | 4 | 16 | 32 | 32 | 16 | 64 |
| 8b) | LiF | 4 | 16 | 32 | 16 | 16 | 64 |
| 9a) | CAFTAZIDIME + | 4 | 4 | 4 | 2 | 4 | 32 |
| 9b) | LiF | 2 | 4 | 4 | 2 | 4 | 34 |

| ANTIBIOTIC | STRAIN Tic S βLac⁻ MIC (mg/l) | STRAIN Tic R βLac⁺ MIC (mg/l) | STRAIN Tic R βLac⁺ MIC (mg/l) | | | |
|---|---|---|---|---|---|---|
| | | | TEM | PSE | OXA | CEPHALOSPORINASE |
| TICARCILLIN | 32 | 512 | 1624 | 4096 | 512 | 256 |
| BENZALKONIUM CHLORIDE + | 32 | 64 | 32 | 64 | 64 | 128 |
| KATHON CG$^R$ (1 mg/l) + | 16 | 32 | 32 | 64 | 32 | 128 |

-continued

| ANTIBIOTIC | STRAIN Tic S βLac⁻ MIC (mg/l) | STRAIN Tic R βLac⁺ MIC (mg/l) | STRAIN Tic R βLac⁺ MIC (mg/l) | | | |
|---|---|---|---|---|---|---|
| | | | TEM | PSE | OXA | CEPHALOSPORINASE |
| KATHON CG$^R$ + (1 mg/l) | 16 | 16 | 32 | 32 | 16 | 32 |

A big improvement is hence observed in the presence of lithium fluoride, this being the case even on the strains producing cephalosporinase.

Example 20

The same trial as in Example 19 was performed, but with nonoxinol 9 as the primary active principle: 200 wild-type strains of *Pseudomonas aeruginosa* were also tested. The results are as follows:

| ANTIBIOTIC | STRAIN Tic S βLac⁻ MIC (mg/l) | STRAIN Tic R βLac⁺ MIC (mg/l) | STRAIN Tic R βLac⁺ MIC (mg/l) | | | |
|---|---|---|---|---|---|---|
| | | | TEM | PSE | OXA | CEPHALOSPORINASE |
| TICARCILLIN | 32 | 512 | 1024 | 4096 | 512 | 256 |
| NONOXINOL 9 + | 64 | 128 | 128 | 64 | 128 | 256 |
| KATHON CG$^R$ (1 mg/l) + | 32 | 128 | 128 | 64 | 128 | 256 |
| KATHON CG$^R$ + LiF (1 mg/l) | 32 | 64 | 64 | 64 | 64 | 128 |

Example 21

The activity of CEFOTAXIME was tested, alone and then in the presence of lithium fluoride, with respect to pathogenic strains other than *Pseudomonas aeruginosa*.

The following table expresses the concentrations (mg/l) of cefotaxime inhibiting 50% of the strains.

| STRAIN | 50% INHIBITORY CONCENTRATION OF CEFOTAXIME ALONE | 50% INHIBITORY CONCENTRATION OF CEFOTAXIME IN THE PRESENCE OF LiF at 1 mg/l |
|---|---|---|
| *Escherichia coli* K12 J53 | 0.023 | 0.01 |
| *Escherichia coli* K12 PIP 111 | 0.023 | 0.023 |
| *Escherichia coli* K12 PIP 55 | 0.023 | 0.023 |
| *Escherichia coli* SOL | 0.18 | 0.18 |
| Klebsiella 1103 | 0.023 | 0.01 |
| Klebsiella U28 | 0.28 | 0.16 |
| Enterobacter T45 | 0.05 | 0.023 |
| Enterobacter P49 | 27.2 | 23.2 |
| *Proteus morganii* F20 | 0.01 | 0.01 |
| Serratia 1123 | 0.076 | 0.076 |
| Serratia MO1117 | 0.30 | 0.30 |

Example 22

The antibiotic activity of amoxicillin (type A penicillin), alone or combined with lithium fluoride, was tested with respect to hospital strains of *Haemophilus influenzae* producing β-lactamase.

The methodology employed is the same as above. The concentration of amoxicillin alone inhibiting the strains to 100% varied between 32 ppm and 64 ppm.

A concentration of 6 ppm of amoxicillin in the presence of 8 ppm of lithium fluoride enabled the strains to be inhibited to 100% in a time varying between 10 and 12 hours.

By way of comparison, a concentration of amoxicillin of 4 ppm in the presence of 1 ppm of clavulanic acid obtained, for example, by the proprietary pharmaceutical product known as AUGMENTIN and marketed by Laboratoires BEECHAM-SEVIGNE (Paris, France) enabled the strains to be inhibited to 100% in 24 hours.

It is hence found that the combination of LiF with amoxicillin enables the threshold of sensitivity of 16 ppm for *Haemophilus influenzae* to be crossed.

Example 23

The antibiotic activity of amoxicillin, alone or combined with lithium fluoride, was tested with respect to hospital strains normally resistant to amoxicillin (inhibitory concentration greater than 16 ppm).

| STRAIN | 100% INHIBITORY CONCENTRATION OF AMOXICILLIN (ppm) | 100% INHIBITORY CONCENTRATON OF AMOXICILLIN IN THE PRESENCE OF LITHIUM FLUORIDE (LiF) | |
|---|---|---|---|
| | | Amoxicillin (ppm) | LiF (ppm) |
| *Staphylococcus aureus* | 32 | 8 | 8 |
| β-*Haemolytic streptococcus* | 16 | 4 | 8 |
| *Klebsiella* | 64 | 2 | 8 |

| STRAIN | 100% INHIBITORY CONCENTRATION OF AMOXICILLIN (ppm) | 100% INHIBITORY CONCENTRATON OF AMOXICILLIN IN THE PRESENCE OF LITHIUM FLUORIDE (LiF) | |
|---|---|---|---|
| | | Amoxicillin (ppm) | LiF (ppm) |
| pneumoniae Haemophilus influenzae | >128 | 32 | 8 |
| Escherichia coli (TEM plasmid) | >128 | 32 | 8 |

Example 24

The antibiotic activity of amoxicillin (type A penicillin of the beta-lactam family), alone or in the presence of lithium fluoride, was tested with respect to various stains.

The results are as follows:

| STRAIN | MINIMAL INHIBITORY CONCENTRATION OF | MINIMAL INHIBITORY CONCENTRATIONS OF AMPICILLIN IN THE PRESENCE OF LITHIUM FLUORIDE (LiF) | |
|---|---|---|---|
| | AMPICILLIN IN mg/l | Ampicillin in mg/l | LiF in mg/l |
| Escherichia coli ATCC 25 922 | 4 | 2 | 1 |
| Streptococcus faecalis ATCC 25 212 | 8 | 4 | 5 |
| Escherichia coli (10 wild-type strains) | 2–8 | 1–4 | 5 |
| Streptococcus faecalis (10 wild-type strains) | 4–8 | 2 | 5 |
| Group C streptococcus | 32 | 8 | 1 |
| Pseudomonas aeruginosa | 16–32 | 4–8 | 5 |

| STRAINS RESISTANT TO AMPICILLIN | MINIMAL INHIBITORY CONCENTRATION OF | MINIMAL INHIBITORY CONCENTRATIONS OF AMPICILLIN IN THE PRESENCE OF LITHIUM FLUORIDE (LiF) | |
|---|---|---|---|
| | AMPICILLIN IN mg/l | Ampicillin in mg/l | LiF in mg/l |
| Haemophilus influenzae (5 wild-type strains) | >128 | 32 | 5 |
| Staphylococcus aureus (10 strains) | >128 | 64 | 1 |
| Staphylococcus aureus (strains producing beta-lactamase) | >128 | 64 | 6 |
| Entrococcus faecium | >128 | 64 | 5 |
| Resistant Escherichia coli | 64 | 8 | 5 |

| MULTIRESISTANT STRAINS OFTEN PRODUCING BETA-LACTAMASE | MINIMAL INHIBITORY CONCENTRATION OF | MINIMAL INHIBITORY CONCENTRATIONS OF AMPICILLIN IN THE PRESENCE OF LITHIUM FLUORIDE (LiF) | |
|---|---|---|---|
| | AMPICILLIN IN mg/l | Ampicillin in mg/l | LiF in mg/l |
| Pseudomonas aeruginosa | 16–32 | 4–8 | 0.8 |
| Escherichia coli | 64 | 8 | 0.8 |
| Staphylococcus aureus | >128 | 32 | 0.8 |
| Group C Streptococcus | 256 | 64 | 0.8 |
| Haemophilus influenzae | >128 | 32 | 0.8 |

Example 25

COMBATING BRONCHOPULMONARY INFECTIONS

The same trials as in Examples 22 and 23 were carried out with tetracycline (cycline family), alone or in the presence of lithium fluoride, on wild-type hospital strains responsible for bronchopulmonary infections.

| STRAIN | 100% INHIBITORY CONCENTRATION OF TETRACYCLINE (ppm) | 100% INHIBITORY CONCENTRATIONS OF TETRACYCLINE IN THE PRESENCE OF LITHIUM FLUORIDE (LiF) | |
|---|---|---|---|
| | | Tetracycline (ppm) | LiF (ppm) |
| Haemophilus influenzae | 4–8 | 2–4 | 4 |
| Klebsiella pneumoniae | 0.5 | 0.25 | 2 |

Example 26
COMBATING SKIN INFECTIONS

The same trials as in Examples 22, 23 and 25 were carried out on wild-type hospital strains responsible for skin infections with, on the one hand polymyxin 8 alone or in the presence of lithium fluoride, and on the other hand erythromycin (macrolide family), alone or in the presence of lithium fluoride.

The results are as follows:

| STRAIN | 100% INHIBITORY CONCENTRATION OF POLYMIXIN B (ppm) | 100% INHIBITORY CONCENTRATIONS OF POLYMIXIN B IN THE PRESENCE OF LITHIUM FLUORIDE (LiF) | |
|---|---|---|---|
| | | Polymixin B (ppm) | LiF (ppm) |
| Group C streptococcus | >128 | 64 | 8 |
| Escherichia coli | >128 | 64 | 2 |
| Staphylococcus aureus | >128 | 64 | 2 |

| STRAIN | 100% INHIBITORY CONCENTRATION OF ERYTHROMYCIN (ppm) | 100% INHIBITORY CONCENTRATIONS OF ERYTHROMYCIN IN THE PRESENCE OF LITHIUM FLUORIDE (LiF) | |
|---|---|---|---|
| | | Erythromycin (ppm) | LiF (ppm) |
| Group C streptococcus | 0.25 | 0.125 | 4 |
| Escherichia coli | 64 | 32 | 8 |

The various examples above show that the addition of lithium fluoride with certain antibiotics makes it possible to envisage the oral or parenteral administration of these antibiotics for combating pathogenic organisms which could not be effectively destroyed previously.

The invention hence relates to an antibiotic product that is administrable, in particular, orally, intravenously or, where appropriate, endolymphatically, characterized in that it contains, on the one hand of the order of 10 mg of lithum fluoride in 10 milliliters of injectable solution, and on the other hand an antibiotic, and an antibiotic product that is administrable intravenously, characterized by concentrations compatible with the physicochemical characters of the components and their possible toxicity.

Example 27

The use of antibiotic agents in chemical antibiotherapy is limited because of the presence of some strains having a resistant phenotype. Those strains would necessitate the use of amounts which cannot be administered to patients because of secondary effects and/or toxicity.

The following trials show that the combination of Fli as activator with an antibiotic agent such as gentamicine changes the phenotype from resistant to sensible, so that the resistant strains may be clinically combated with this combination.

The strains used were wild-type hospital strains having a resistant phenotype as regards gentamicine: *pseudomonas aeruginosa, proteus mirabilis, serratia marcescens*.

The phenotype of the strains was determined by diffusion in gradient on selective agar. Then, each group of strains having the same phenotype (resistant or sensible) was seeded on inclined agar having a gradient of concentration of the composition.

This methodology is explained by SZYBALSKI and BRYSON in "Selected de mutants resistant aux antibiotiques", L'antibiogramme, Vigot, p. 259–260.

The results are shown in the following table illustrating the MIC of gentamicine (aminoglycoside antibiotic).

x/y means a concentration read between x ppm and y ppm.

| STRAIN | PSEUDOMONAS AERUGINOSA | PROTEUS MIRABILIS | SERRATIA MARCESCENS |
|---|---|---|---|
| MIC (ppm or mg/l) alone on the strains before separation of the phenotypes | 64/128 | 32/64 | 32/64 |
| MIC (ppm or mg/l) of gentamicine alone on SENSIBLE strains | 32/64 | 16/32 | 16/32 |
| MIC (ppm or mg/l) of Fli alone on SENSIBLE strains | >32 | >32 | >32 |
| MIC (ppm or mg/l) of gentamicine in presence of Fli (ppm or mg/l) on SENSIBLE strains | 16/32 (Fli at 8/16) | 4/8 (Fli at 4/8) | 8 (Fli at 8) |
| MIC (ppm or mg/l) of gentamicine alone on RESISTANT strains | 256/512 | 64/128 | 128/256 |
| MIC (ppm or mg/l) of gentamicine in presence of Fli (ppm or mg/l) on RESISTANT strains | 64 (Fli at 16) | 16/32 (Fli at 8/16) | 32 (Fli at 16) |

Therefore, the MIC of gentamicine in presence of Fli on resistant strains is lowered to values similar to the MIC on sensible strains, and a synergistic effect is obtained by the combination of gentamicine and Fli on sensible strains.

It is possible to clinically administrate the antibiotic even in presence of resistant strains, and with amounts 50% lower in presence of Fli than the amounts needed with gentamicine alone.

This synergistic activation of Fli has also been similarly demonstrated on other families of antibiotic agents.

Example 28

The synergistic effect of the combination of Fli with an antibiotic agent has been shown by the "chess" test which is a known methodology of dilution in liquid medium (Microdilution transportplate technic for determining in vitro synergy of antimicrobial agents"—DOUGHERTY P. F.

Antimicrobial Agent Chemotherapy n° 9.225 228, 1977, or "In vitro activity synergism and testing parameters of amikacyn with comparisons to other aminoside antibiotics" KELLY M. T. Antimicrobial Agents Chemotherapy n° 9.440 447, 1976). Concentration series of two antibiotic substances A and B are prepared in the geometric ratio of 2 are combined and the following values are determined:

MIC A=minimal inhibiting concentration of A alone
MIC B=minimal inhibiting concentration of B alone
MIC A/B=minimal inhibiting concentration A in presence of B
MIC B/A=minimal inhibiting concentration B in presence of A $$FIC \text{ (Fractionnal Inhibiting Concentration)} = \frac{MIC\ A/B}{MIC\ A} + \frac{MIC\ B/A}{MIC\ B}$$

The MIC of the bacteriostatic effect is read when the percentage of surviving strains is less or equal to 1%.

The combination of the substances A and B is synergistic as regards the bacteriostatic effect when $FIC \leq 0.75$. The combination is additive when $FIC=1$. The combination is insensible when $1 < FIC \leq 2$. The combination is antagonistic when $FIC > 2$.

Trial 1

Substance A was tetracycline (concentration serie from 0.25 to 128 mg/l)

Substance B was Fli (concentration serie from 0.25 to 16 mg/l)

The strain was *staphylococcus aureus* (wild-type hospital resistant strain)

It was found that:

MIC A=32 mg/l
MIC B=64 mg/l
MIC A/B=4 mg/l
MIC B/A=16 mg/l
FIC=0.375

The combination is thus demonstrated as synergistic.

Trial 2
  Substance A was gentamicine
  Substance B was Fli
  The strain was a very resistant *proteus mirabilis* (wild-type hospital)

MIC A=64 mg/l
MIC B=128 mg/l
MIC A/B=16 mg/l
MIC B/A=16 mg/l
FIC=0.375

Trial 3
  Substance A was gentamicine
  Substance B was Fli
  The strain was *Klebsiella pneumoniae* (wild-type hospital strain)

MIC A=16 mg/l
MIC B=128 mg/l
MIC A/B=4 mg/l
MIC B/A=32 mg/l
FIC=0.5

The combination is thus demonstrated as synergistic.

Trial 4
  Substance A was gentamicine
  Substance B was Fli

The strain was *pseudomonas aeruginosa* (wild-type hospital resistant strain)

MIC A=64 mg/l
MIC B=128 mg/l
MIC A/B=16 mg/l
MIC B/A=16 mg/l
FIC=0.375

Example 29

It is known that a strain develops a resistance against an antibiotic substance with which it is left in contact, by a phenotypical mutation procedure.

This phenomena has been studied on *Pseudomonas aeruginosa* and *Escherichia coli* (wild-type hospital strains) which commonly develop resistance against aminosides. The antibiotic substance choosen was thus gentamicine which is an aminoside antibiotic.

And the growth of the resistance was studied with gentamicine alone, then with gentamicine in presence of Fli.

The trial was conducted on 12 days, and the MIC of gentamicine alone and of gentamicine in presence of Fli (4 ppm) was determined each day on transportplates in liquid medium with a serie of dilution in Mueller/Hinton agar.

The MBC (Minimal Bactericide Concentration) was also determined from the solution after determination of the MIC seeded on agar adapted to the strain. The MBC is read for a percentage of survivors less than 0,20%.

FIG. 1 illustrates the curves of the MIC of gentamicine alone, Fli, and gentamicine in presence of Fli (4 ppm) for *pseudomonas aeruginosa*.

FIG. 2 illustrates the curves of the MIC of gentamicine alone, Fli, and gentamicine in presence of Fli (4 ppm) for *escherichia coli*.

FIG. 3 illustrates the curves of the MBC of gentamicine alone and gentamicine in presence of Fli (4 ppm) for both strains.

It appears that no resistance is developped by the strain against Fli, but a resistance corresponding to 8 to 16 times the initial MIC is developped by gentamicine alone, the third or fourth day.

In presence of gentamicine with Fli (4 ppm) the resistance appears later (the fourth or sixth day) an only corresponds to 4 to 8 times the initial MIC.

Therefore the presence of Fli retards the creation of the resistance and reduces to the half the capability of each strain for developping such resistances.

Example 30

The kinetics of the bacterial growth of *serratia marcescens* and *salmonella spirochete* has been studied with the "Time killing curve" methodology, for gentamicine (64 ppm) alone, Fli (32 ppm) and gentamicine (64 ppm) in presence of Fli (32 ppm). The bacterial growth is determined by spectrophotometric reading of the optical density for a wavelength of 600 nm.

The following table illustrates the optical density (1/100) obtained:

| STRAIN | | 0 h 00 | 3 h 00 | 6 h 00 | 24 h 00 |
|---|---|---|---|---|---|
| SERRA- | INOCULUM | 8,5 | — | — | — |
| TIA | GROWTH SAMPLE | — | 36 | 45 | 49 |
| MARCE- | GENTAMICINE | — | 5,5 | 5 | 4 |
| SCENS | Fli | — | 13 | 15 | 18 |
| | GENTAMICINE + Fli | — | 2,5 | 1,5 | 0,7 |
| SAL- | INOCULUM | 11 | — | — | — |
| MON- | GROWTH SAMPLE | — | 29 | 37 | 44 |
| ELA | GENTAMICINE | — | 8 | 7 | 5,5 |
| | FLi | — | 14 | 14,5 | 20 |
| | GENTAMICINE + Fli | — | 5 | 3 | 1,5 |

FIG. 4 illustrates the time killing curves obtained for *serratia marcescens*.

FIG. 5 illustrates the time killing curves obtained for *salmonella spirochete*.

It is thus shown a synergistic activity of gentamicine combined with Fli.

Example 31

The MIC of tetracycline was studied on *Klebsiella pneumoniae* (wild-type hospital strain).

The trial was conducted with tetracycline alone, tetracycline in presence of FNa and tetracycline in presence of Fli.

| | TETRACYCLINE alone | TETRACYCLINE + FNa (8 ppm) | TETRACYCLINE + Fli (8 ppm) |
|---|---|---|---|
| MIC (ppm) | 512 | 256/512 | 128 |

It is thus demonstrated a better unexpected activation of tetracycline by Fli than by FNa.

Example 32

The MIC of doxycycline was studied on *pseudomonas aeruginosa* (wild-type hospital strain) in the same conditions as for example 31.

| | DOXYCYCLINE alone | DOXYCYCLINE + FNa (8 ppm) | DOXYCYCLINE + Fli (8 ppm) |
|---|---|---|---|
| MIC (ppm) | 1000 | 500/1000 | 256/500 |

Thus Fli is a surprisingly better activator of doxycycline than Fna.

Example 33

The efficiency in vivo of the administration of doxycycline in presence of Fli has been measured and compared with the efficiency of the administration of doxycycline alone.

The antibiotic composition (doxycycline alone or with Fli) has been administered to a healthy patient, and the antibiotic activity of the patient's blood has been determined before the first administration, the day of the administration, and three days later. The delay of three days is necessary because of the low solubility of Fli: the pertinent concentration of Fli is only obtained after the end of the second day after its administration.

The patient has taken the antibiotic during the thee days, 2 capsules of 250 mg each day at 8 a.m. A blood sample was taken 3 hours after each administration.

And the antibiotic activity was twice determined by a microbiological titration using the inhibition holes methodology on a standard strain ATCC 25922 of *Escherichia coli*.

Holes of 6 mm diameter were made on a Mueller Hinton agar and 100 µl of plasma were injected in each hole. The agar was then seeded with an inoculum of *Escherichia coli* of 10 UFC/ml.

After an incubation of 24 hours at 37° C., the diameters around each holes (in which the strain was killed) were read.

In the first trial, the capsules of 250 mg were constituted of 110 mg of doxycycline chlorohydrate and of lactose.

The inhibition diameters were measured as follows

J 0=the day before the first administration
J 1=the day of the first administration
J 3=the third day of administration

| DAY OF MEASURE | INHIBITION DIAMETER (mm) DOXYCYCLINE ALONE |
|---|---|
| J 0 | 7 |
| J 1 | 8–9 |
| J 3 | 11–12 |

The second trial was conducted similarly with gelules of 250 mg constituted of 110 mg of doxycycline, 53 mg of Fli and lactose.

| DAY OF MEASURE | INHIBITION DIAMETER (mm) DOXYCYCLINE + Fli |
|---|---|
| J 0 | 7 |
| J 1 | 10–11 |
| J 3 | 14–15 |

Therefore the better antibiotic activity of the activated antibiotic is demonstrated in vivo.

Example 34

Clinical experiments on ill patients were conducted with antibiotic compositions activated with Fli.

The antibiotic agent dose in 250 mg capsules was lowered to 60% of the normally administered dose (defined by VIDAL DICTIONARY, France, 1987), and an appropriate dose of Fli was added. The activated capsules were administered with the same methodology as for the non-activated antibiotic capsules (as indicated in the VIDAL DICTIONARY).

The appropriate dose of Fli was defined to have an amount of lithium in the blood of 1,5 ppm after 2 hours. Thus, when only one capsule is administered per day (for example for doxyclycline) an approximative dose of 50 mg of Fli is used in the capsule. When two capsules are administered per day (for example for bactrim (registered trademark) the dose of Fli per capsule is about 25 mg.

47 experiments were conducted on patients who had caught pneumopathies such as bronchitis, or cystisis due to staphylococci. Various kinds of antibiotic agents were used: doxycycline, amoxicilline, spiramycine, tetracycline, josamycine, bactrim (registered trademark) (sulfamide+ diaminopyrimidine).

No case of intolerance was observed.

Only one check was met with a 65 years old patient attacked by bronchitis treated with activated spiramycine. All the other patients were cured in 4 to 6 days of treatment, though the antibiotic dose was only 60% the normally prescribed dose.

Furthermore some of the patients thus cured had been attacked by chronicle affections or had been previously treated by a firts standard antibiotic treatment without success.

Therefore the surprising efficiency of the activation by Fli has been clinically demonstrated in vivo.

Example 35

Strains Gram+ and Gram– (wild-type hospital) having a resistant phenotype vis a vis standard firstly and secondly used antibiotherapy were experimented on activated antibiotics.

250 experiments were conducted on the following strains: Streptococcus group B, C, D, F, G, *Staphylococcus aureus, Staphylococcus epidermitis, Klebsiella pneumoniae, Klebsiella Spirochete, Klebsiella oxytoca, Proteus mirabilis, Serratia macescens, Escherichia coli, Citrobacter freundii, Enterobacter cloacae, Enterobacter calcoaceticus, Salmonella spirochete, Salmonella typhimurium, Pseudomonas aeruginosa, Haemophilus influenzae, Haemophilus aphrophilus, Acinetobacter calcoaeticus.*

The antibiotic agents used were (depending on each strain, the 10 to 20 antibiotic agents commonly used on the strains were experimented without Fli and in presence of Fli at 4 ppm): Penicilline (group G), Ampicilline, Erythromicine, Tetracyline, Amoxicilline, Doxycycline, Minocycline, Trimethoprime, Josamycine, Streptomycine, Gentamicine, Cefazoline, Chloramphenical, Framycetine, Bactrim (registered trademark), Thiamphenical, Pristinamycine, Lincomycine, Troleandomycine, Oxacilline, Cefalotine, Mexlocilline, Cefalexine, Cefotazime, Amoxicilline+clavulanic acid, Lymecycline, Netilmicine, Nalidixic acid, Pefloxacine, Tobramycine, Amikacine, Norfloxacine, Cefsulodine, Polymixine B, Cefoperazone, Kanamycine, Midecamycine, Nitrofurantoine, Cotrimoxazole, Ticarcilline, Piperacilline, Oflozacine, Fosfomycine, Ticarcilline+clavulanic acid. Therefore all the families of antibiotic agents were experimented.

The results of the experiments have been given in term of phenotype: resistant when the MIC is superior to a given threshold value (depending on the antibiotic agent, commonly about 16 ppm), insensible when the MIC is inferior to the around the threshold value, sensible when the MIC is inferior to the threshold value.

In the case of streptococcus group F with penicilline group G, the insensible phenotype was not changed by the presence of Fli (4 ppm).

In the case of *Klebsiella pneumoniae* with cefoperazone and *staphylococcus aeurus* with amoxicilline or erythromycine the resistant phenotype was not changed by the presence of Fli (4 ppm).

In all the other cases, the phenotype changed from resistant or insensible to insensible or sensible.

In 145 experiments, the strain became totally sensible vis a vis the activated antibiotic. And 73 totally resistant strains were even changed to totally sensible with the activation by Fli. The other totally resistant strains representing 76 experiments were changed to insensible strains.

It is thus possible with the invention to combat some resistant pathogen microorganism, where this was not possible with classical antibiotherapy. The mere activation of antibiotics with 4 ppm of Fli, which is a totally innocuous dose, surprisingly allows the curation of high resistant strains such as *haemophilus influenzae, Klebsiella pneumoniae* or others.

It is noted that an "antibiotic" agent may be described as a germicidal agent which can be introduced into the human or animal body at such concentrations that it can maintain its efficacy without any resultant toxicity or side effects.

What is claimed is:

1. A method for treating diseases caused by pathogenic bacterial microorganisms in a human or an animal, which method comprises administering to said human or animal an antibiotic composition which comprises an effective amount of ionic or ionizable lithium.

2. The method for treating diseases caused by pathogenic bacterial microorganisms in a human or an animal as in claim 1, which method comprises administering to said human or animal an antibiotic composition which further comprises effective amounts of ionic or ionizable fluorine.

3. The method for treating diseases caused by pathogenic bacterial microorganisms in a human or an animal as in claim 1, which method comprises administering to said human or animal an antibiotic composition wherein the ionic or ionizable lithium and fluorine are present in the form of lithium fluoride and which composition further comprises a suitable excipient.

4. The method for treating diseases caused by pathogenic bacterial microorganisms in a human or an animal as in claim 3, which method comprises administering to said human or animal an antibiotic composition which further comprises an effective amount of a spermicidal agent.

5. The method for treating diseases caused by pathogenic bacterial microorganisms in a human or an animal as in claim 1, which method comprises administering to said human or animal an antibiotic composition wherein the spermicidal agent is selected from the group consisting of benzalkonium chloride or nonoxynol, and which composition further comprises a preservative agent.

6. The method as claimed in claim 5 for treating diseases caused by pathogenic bacterial microorganisms in a human or an animal, wherein the composition further comprises an additional fluorine salt.

7. A method for treating diseases caused by pathogenic bacterial microorganisms in a human or an animal, which method comprises administering to said human or animal an antibiotic composition comprising an effective amount of ionic or ionizable fluorine, an effective amount of ionic or ionizable lithium and an effective amount of an antibiotic agent.

8. The method as claimed in claim 7 wherein said antibiotic agent in said composition is selected from the group consisting of betalactamins, macrolides, polypeptidic antibiotics, phenicolated antibiotics, rifamycins, lincosanides, streptogramines, sulfamides, trimethoprimes, aminocides, cyclins, quinolones and their derivatives and combinations thereof.

9. A composition comprising effective amounts of ionic or ionizable lithium and an antibiotic agent, which antibiotic agent is selected from eh group consisting of betalactamins, macrolides, polypeptidic antibiotics, phenicolated antibiotics, rifamycins, lincosanides, streptogramines, sulfamides, trimethoprimes, aminocides, cyclins, quinolones and their derivatives and combinations thereof.

10. The composition as claimed in claim 9, which further comprises ionic or ionizable fluorine.

11. The composition as claimed in claim 10, which further comprises lithium fluoride.

12. The composition as claimed in claim 11, which further comprises a suitable excipient.

* * * * *